US 7,975,721 B2

(12) United States Patent
Hiebert

(10) Patent No.: US 7,975,721 B2
(45) Date of Patent: Jul. 12, 2011

(54) FLUID VALVE SYSTEMS

(76) Inventor: John Hiebert, Wayland, MA (US)

( * ) Notice: Subject to any disclaimer, the term of this patent is extended or adjusted under 35 U.S.C. 154(b) by 835 days.

(21) Appl. No.: 11/692,401

(22) Filed: Mar. 28, 2007

(65) Prior Publication Data

US 2008/0275398 A1    Nov. 6, 2008

Related U.S. Application Data

(60) Provisional application No. 60/786,883, filed on Mar. 30, 2006.

(51) Int. Cl.
*F16K 11/16* (2006.01)
*F17D 1/14* (2006.01)
*A61M 1/00* (2006.01)
*A61M 5/145* (2006.01)

(52) U.S. Cl. ......... 137/625.29; 137/625.47; 137/599.03; 137/599.11; 604/32; 604/248

(58) Field of Classification Search ............ 137/606, 137/607, 625.28, 625.29, 652.47, 205.5, 137/268, 599.3, 599.12, 596.12, 599.11, 137/15.05, 565.33; 604/131, 32, 248
See application file for complete search history.

(56) References Cited

U.S. PATENT DOCUMENTS

| 2,485,824 | A | * | 10/1949 | Gladstone ............... 84/422.4 |
| 2,485,842 | A | | 10/1949 | Pennington |
| 2,758,877 | A | * | 8/1956 | Gleason ................ 422/113 |
| 2,854,027 | A | | 9/1958 | Kaiser et al. |
| 3,416,567 | A | | 12/1968 | Von Dardel et al. |
| 3,476,137 | A | * | 11/1969 | Eisendrath ............... 137/268 |
| 3,861,388 | A | | 1/1975 | Vaughn |
| 4,241,761 | A | | 12/1980 | Miller |
| 4,256,135 | A | | 3/1981 | Hannah |
| 4,257,416 | A | | 3/1981 | Prager |
| 4,285,365 | A | | 8/1981 | Coats et al. |
| 4,397,335 | A | | 8/1983 | Doblar et al. |
| 4,439,182 | A | | 3/1984 | Huang |
| 4,623,334 | A | | 11/1986 | Riddell |
| 4,819,694 | A | | 4/1989 | Jiang |
| 4,915,688 | A | * | 4/1990 | Bischof et al. ............... 604/83 |
| 5,056,549 | A | | 10/1991 | Bouilloux et al. |
| 5,105,851 | A | | 4/1992 | Fogelman |
| 5,113,904 | A | | 5/1992 | Aslanian |
| 5,135,026 | A | | 8/1992 | Manska |
| 5,336,201 | A | | 8/1994 | von der Decken |
| 5,340,364 | A | | 8/1994 | Ghelli et al. |
| 5,466,228 | A | | 11/1995 | Evans |
| 5,466,480 | A | | 11/1995 | Zhou et al. |

(Continued)

OTHER PUBLICATIONS

U.S. Appl. No. 10/816,751, filed Apr. 2, 2004, Hiebert.

(Continued)

*Primary Examiner* — Stephen M Hepperle
*Assistant Examiner* — Atif H Chaudry
(74) *Attorney, Agent, or Firm* — Finch & Maloney PLLC

(57) ABSTRACT

An apparatus includes a first valve having an inlet capable of being in fluid communication with a first fluid source, an outlet capable of being in fluid communication with the inlet, and two unidirectional valves. The first valve is capable of being in a first mode in which the inlet is in fluid communication with the outlet through a first flow path, and a second mode in which the inlet is in fluid communication with the outlet through a second flow path isolated from the first flow path. The two unidirectional valves are along the second flow path.

24 Claims, 9 Drawing Sheets

U.S. PATENT DOCUMENTS

| | | | |
|---|---|---|---|
| 5,713,850 | A | 2/1998 | Heilmann et al. |
| 5,807,312 | A | 9/1998 | Dzwonkiewicz |
| 5,817,068 | A | 10/1998 | Urrutia |
| 5,832,959 | A | 11/1998 | Szymczakowski et al. |
| 5,839,470 | A | 11/1998 | Hiejima et al. |
| 5,848,611 | A | 12/1998 | Stanevich |
| 6,135,153 | A | 10/2000 | Cleland, Sr. et al. |
| 6,173,732 | B1 * | 1/2001 | Davis et al. .................. 137/377 |
| 6,394,980 | B2 | 5/2002 | Kriesell et al. |
| 6,418,966 | B2 | 7/2002 | Loo |
| 6,457,488 | B2 | 10/2002 | Loo |
| 6,481,462 | B2 | 11/2002 | Fillmore et al. |
| 6,612,337 | B2 | 9/2003 | Su |
| 6,708,948 | B2 | 3/2004 | Nosel |
| 6,726,656 | B2 | 4/2004 | Kamen et al. |
| 6,918,893 | B2 | 7/2005 | Houde et al. |
| 6,953,450 | B2 | 10/2005 | Baldwin et al. |
| 2001/0051791 | A1 | 12/2001 | Azzolini |

OTHER PUBLICATIONS www.icumed.com 102® Fluid Delivery System, Directions for use, ICU Medical, Inc., San Clemente, CA, Oct. 2003, 2 pages.

The Easy to Use 4-Port Stopcock, "The Twist-N-Ject™" Stopcock, The 4-Port Stopcock, G.L. Medical, Beverly Hills, CA, 2 pages.

www.elcam-medical.com Induction/Sampling Manifold, On-Demand Induction, Elcam Medical, Inc., Phoenix, Arizona, 1 page.

PCT International Search Report and Written Opinion for PCT Application No. PCT/US07/82853 mailed on Apr. 18, 2008, 10 pages.

* cited by examiner

FLUID VALVE SYSTEMS

CLAIM OF PRIORITY

This application claims priority to U.S. Provisional Patent Application No. 60/786,883, filed on Mar. 30, 2006, and entitled "Fluid Valve System", hereby incorporated by reference in its entirety.

FIELD OF THE INVENTION

The invention relates to fluid valve systems, such as an apparatus for controlling the intravenous administration of fluid.

BACKGROUND

In hospitals, it is common to administer fluid and medicaments to patients via the parenteral, or intravenous (IV) route. The vast majority of hospitalized patients and all patients undergoing surgery have an IV catheter placed for delivering medicaments such as antibiotics, emergency resuscitation drugs, for inducing and maintaining anesthesia, and for the infusion of fluid volume and blood products Two broad functional modes define IV systems: continuous infusion and bolus dosing. The bolus mode is used for medications that are safe for rapid administration and intended for immediate bioavailability. Bolus mode is typically quickly accessible within any IV system because patients routinely are given a variety of medication boluses in addition to one or more concurrent infusions. The frequency of bolus drug administration may range from zero to dozens per day. Occasionally, multiple boluses are delivered in rapid succession necessitating repeated switching between modes, as occurs in surgery and interventional procedures, in the intensive care unit (ICU), in the management of unstable patients, and in medical and surgical emergencies.

SUMMARY OF THE INVENTION

The invention relates to fluid valve systems, such as, for example, IV systems so as to increase safety and efficiency of IV administration of fluid and medicaments.

In one aspect, the invention features an apparatus including an apparatus, including a first valve having an inlet capable of being in fluid communication with a first fluid source; an outlet capable of being in fluid communication with the inlet; and two unidirectional valves, wherein the first valve is capable of being in a first mode in which the inlet is in fluid communication with the outlet through a first flow path, and a second mode in which the inlet is in fluid communication with the outlet through a second flow path isolated from the first flow path, and the two unidirectional valves are along the second flow path.

Embodiments may include one or more of the following features. The first valve further includes a port in fluid communication with the second flow path between the two unidirectional valves. The port is adapted to be in fluid communication with an injector. The first valve is associated with a base, and the injector is capable pivoting relative to the base. The apparatus further includes an injector undetachably attached to the first valve. The apparatus further includes an injector engageable with the first valve, and an enclosure enclosing at least a portion of the injector. The two unidirectional valves are capable of being between the inlet and the outlet along the second flow path. The first valve further includes a controller capable of controlling fluid flow through the first flow path. The first flow path is capable of being in fluid communication with a second fluid source. The first valve includes a body having at least a portion of the first flow path, at least a portion of the second flow path, and the two unidirectional valves, and rotation of the body allows the first valve to be in a selected mode. The first valve includes a body having a first channel, a second channel, and a third channel containing the two unidirectional valves, the first, second and third channels capable of being isolated from each other, wherein, in the first mode, the first channel, the second channel, the inlet, the outlet, and the first flow path are in fluid communication, and in the second mode, the third channel, the inlet, and the outlet are in fluid communication. The first valve further includes a tactile indicator capable of denoting a selected mode of the first valve.

The apparatus can further include a second valve capable of being in fluid communication with the first valve, the second valve including a second inlet, a second outlet capable of being in fluid communication with the second inlet, and a port, wherein the second valve is capable of being in a third mode in which the second inlet is capable of being in fluid communication with the second outlet, and a fourth mode in which the second outlet is capable of being in fluid communication with the port. The second valve can be configured to engage with a fluid injector, and the injector and the port are capable of being in fluid communication. The second valve can be associated with a base, and the injector is capable of pivoting relative to the base. The first and second valves can be secured to a base.

In another aspect, the invention features an apparatus, including a first valve having an inlet capable of being in fluid communication with a first fluid source; an outlet capable of being in fluid communication with the inlet; and two unidirectional valves, wherein the first valve is capable of being in a first mode in which the inlet is in fluid communication with a first flow path, and a second mode in which the inlet is in fluid communication with the outlet through a second flow path isolated from the first flow path, and the two unidirectional valves are along the second flow path; and a second valve capable of being in fluid communication with the first valve, the second valve including a second inlet, a second outlet capable of being in fluid communication with the second inlet, and a port, wherein the second valve is capable of being in a third mode in which the second inlet is capable of being in fluid communication with the second outlet, and a fourth mode in which the second outlet is capable of being in fluid communication with the port wherein the first flow path extends from the inlet of the first valve to a position downstream of the second outlet of the second valve when the first valve is in the second mode.

Embodiments may include one or more of the following features. The apparatus further includes a unidirectional valve along the first flow path. The first valve further includes a port in fluid communication with the second flow path between the two unidirectional valves. The port is adapted to be in fluid communication with an injector. The first valve is associated with a base, and the injector is capable pivoting relative to the base. The two unidirectional valves are capable of being between the inlet and the outlet along the second flow path. The first valve further includes a controller capable of controlling fluid flow through the first flow path. The first flow path is capable of being in fluid communication with a second fluid source. The first valve includes a body having at least a portion of the first flow path, at least a portion of the second flow path, and the two unilateral valves, and rotation of the body allows the first valve to be in a selected mode. The first valve further includes a tactile indicator capable of denoting a selected mode of the first valve.

In another aspect, the invention features a method, including in a first mode, flowing a fluid from an inlet of a first valve to an outlet of the first valve through a first flow path; and in a second mode, unidirectionally flowing the fluid from the inlet to the outlet through a second flow path isolated from the first flow path.

Embodiments may include one or more of the following features. Unidirectionally flowing the fluid from the inlet to the outlet through the second flow path includes flowing the fluid through two unidirectional valves along the second flow path. The method further includes controlling rate of flow through the first flow path. The method further includes introducing a second fluid to the first flow path. The method further includes rotating a body of the valve to select a mode. The method further includes unidirectionally drawing fluid from the inlet into the second flow path. The method further includes unidirectionally delivering fluid from the second flow path to the outlet. The method further includes tactilely detecting a selected mode of the valve. The method further includes flowing the fluid from the outlet to a second valve.

In another aspect, the invention features a method, including in a first mode, flowing a fluid from an inlet of a first valve to a patient without passing the fluid through an outlet of the first valve, the fluid flowing through a first flow path; and in a second mode, unidirectionally flowing the fluid from the inlet to the outlet through a second flow path isolated from the first flow path.

Embodiments may include one or more of the following features. Unidirectionally flowing the fluid from the inlet to the outlet through the second flow path includes flowing the fluid through two unidirectional valves along the second flow path. The method further includes controlling rate of flow through the first flow path. The method further includes introducing a second fluid to the first flow path. The method further includes rotating a body of the valve to select a mode. The method further includes unidirectionally drawing fluid from the inlet into the second flow path. The method further includes unidirectionally delivering fluid from the second flow path to the outlet. The method further includes tactilely detecting a selected mode of the valve. The method further includes flowing the fluid from the outlet to a second valve. In the first mode, fluid flows from the inlet to a location downstream of fluid exiting the second valve. The method further includes unidirectionally flowing fluid through the first flow path.

Embodiments may include one or more of the following advantages.

The valve systems can replace and/or supersede the functions of a four-way stopcock.

The valve systems can conveniently serve the two main functions of an IV infusion system, those being 1) baseline continuous flow from a main IV fluid and any auxiliary IV fluid, and 2) rapid bolus injection and flushing, e.g., of medicament. In some embodiments, the systems achieve the above by incorporating two distinct types of valve: an upstream valve containing two or more mutually exclusive fluid streams which rotates to one position for flush syringe filling and emptying, and another position for constant infusion flow, from the main IV fluid reservoir and any auxiliary IV fluid reservoirs; and a downstream valve which rotates to either of two positions to achieve exclusive bolus injection (e.g., of medicament) or infusion flow from one or more IV infusion bags.

The valve systems can promote safety of patients, for example, 1) by providing one-handed operation, leaving the other hand of the clinician free to perform other tasks; 2) by allowing syringes filled with medicament to remain attached to the medicament injection valves without risking inadvertent injection and without needing to use single valves for multiple purposes, such as flushing or connection of auxiliary infusions; 3) by restricting medicament injection valves to only two rotational settings, neither of which allows medicament to come into contact with the upstream fluid pathway, thereby precluding contamination or dilution of medicament; and/or 4) avoiding inadvertent fluid overload as a result of improved flush technique;

The valve systems can promote safety of clinicians by simplifying the filling of flush syringes, thereby reducing the tendency of a clinician to choose a needle-based method of flush syringe filling;

The valve systems can promote efficiency of clinicians, for example, 1) by providing one-handed operation for all valve functions, including medicament injection, flush syringe filling, and flush syringe emptying; 2) by reducing the number of steps used to inject and flush medicament and by making those steps easier to perform; 3) by permitting full-bore flush syringe filling and emptying without needing to make any prior adjustment to a roller clamp; 4) by permitting flush syringe filling from the main IV fluid without needing to prior clamp any auxiliary IV fluid line; 5) by establishing a uniform and predictable location in the IV setup where auxiliary infusion are intended to be connected; and 6) by allowing valve position to be determined easily by gross visual inspection of the angle of the attached syringe as opposed to looking at the lever position of a conventional stopcock.

The valve systems can be made by press fit assembly of injection molded plastic components to provide a sterile, disposable system. In order to facilitate one-handed operation the valves may be attached to a base of dimensions suitable to allow rotation of the valves by moving the attached syringes while the base serves as anchor. The valves can be attachable in one embodiment by Luer lock connectors so that multiple medicament injection valves may be placed in series downstream from the flush valve.

DETAILED DESCRIPTION

Figure 1:
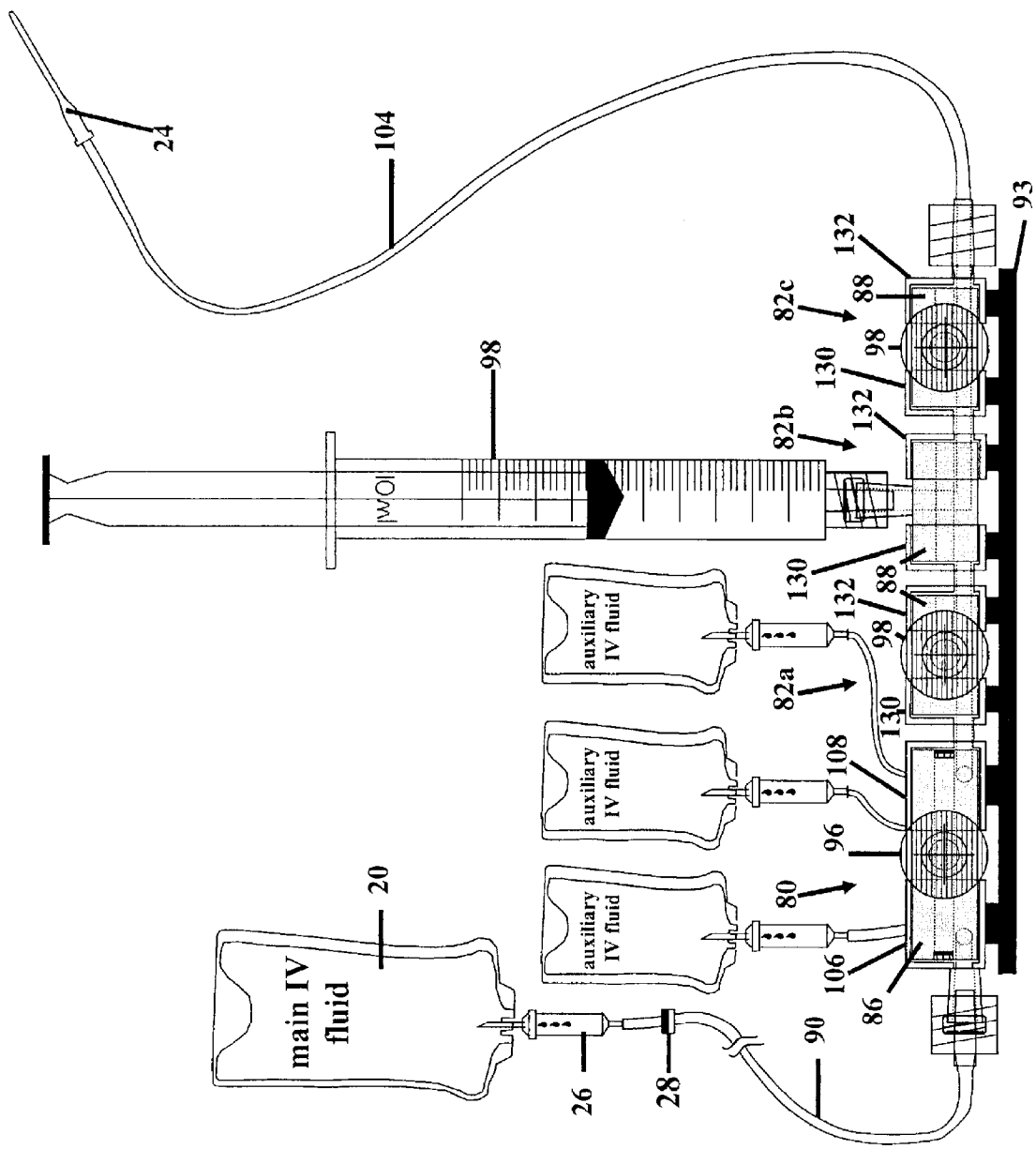
FIG. 1 illustrates a front elevational view of an embodiment of a valve system showing one flush valve and three injection valves, and showing a second injection valve in the injection mode. Elements are not shown in the same scale. Three auxiliary infusions are shown with their tubing leading toward a midstream conduit (not shown) of the flush valve.
Figure 2:
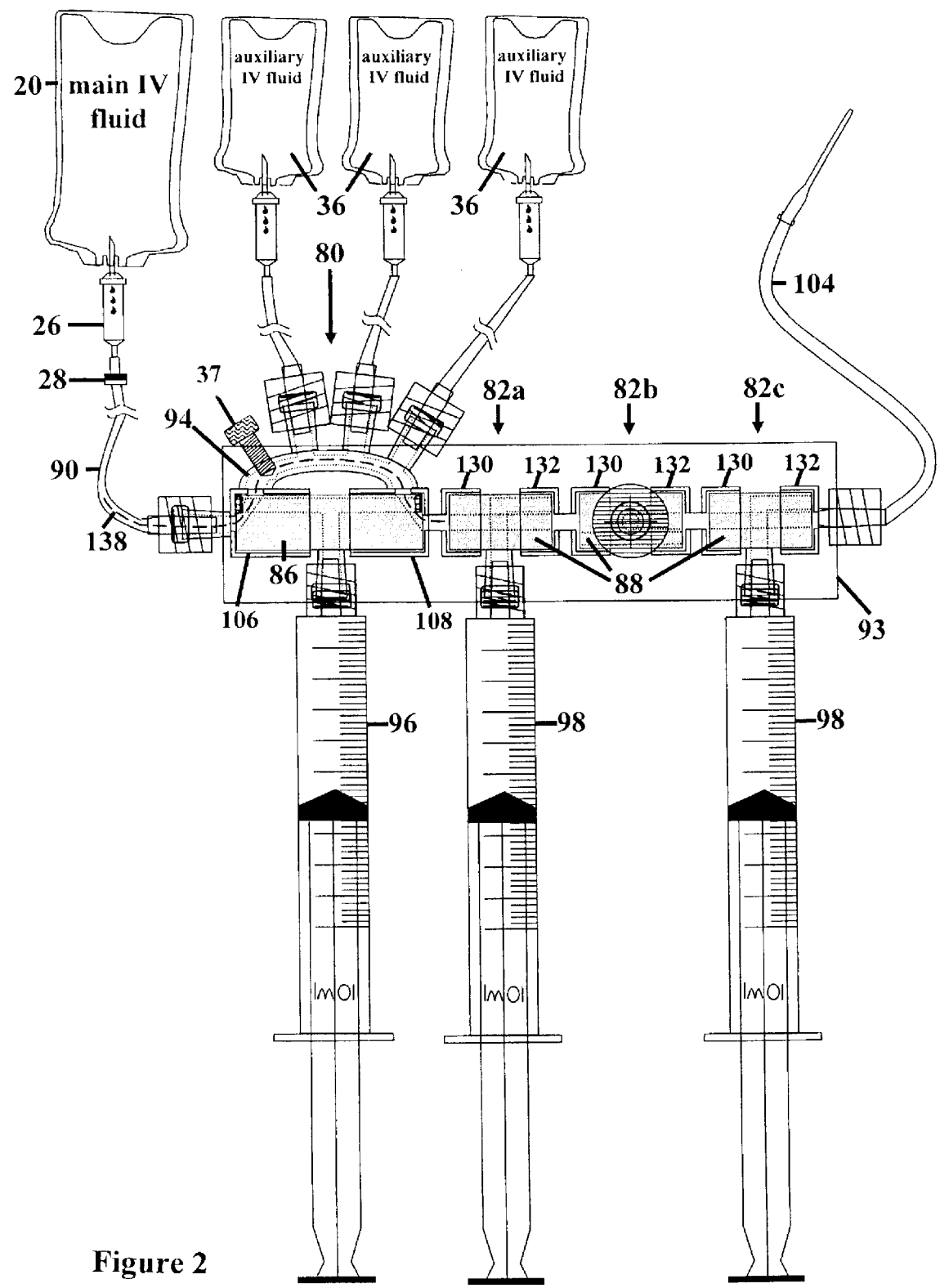
FIG. 2 illustrates a top view of the valve system shown in FIG. 1.

FIGS. 1 and 2 depict an apparatus for regulating fluid flow in an IV administration system FIG. 1 from the front and FIG. 2 from the top. Fluid is received from a main IV fluid reservoir 20 via an upstream conduit 90, and/or from one or more auxiliary IV fluid reservoirs 36. A drip chamber 26 maintains a liquid level of fluid to be administered. Fluid is subsequently delivered to a downstream conduit 104 and onward to a patient (not shown). The apparatus includes two types of cylindrical valve being flush valve 80, and injection valve 82. Three injection valves 82a, 82b, and 82c are shown in FIGS. 1 and 2 arranged in series downstream of the flush valve. Each valve is actuated by movement of a syringe, such as syringes 96 and 98. Syringe 96 is attached to a flush cylinder 86 and syringe 98 is attached to an injection cylinder 88 such that the longitudinal axis of each syringe is perpendicular to the longitudinal axis of its associated cylinder. Any syringe shown in FIGS. 1 and 2 has the exclusive function of a flush syringe 96 or a medicament injection syringe 98, by virtue of the cylinder to which it is attached.

End caps are fluid-tight housings that fit snugly around the ends of the cylinders. The flush valve 80 has an upstream end cap 106 and a downstream end cap 108 positioned on the ends of flush cylinder 86. Injection valves have upstream end caps 130 and downstream end caps 132 positioned on the ends of injection cylinders 88. By moving the syringe in an arc the clinician is able to rotate the attached cylinder, such as cylinder 86 and 88, about its longitudinal axis, causing channels within each cylinder to move relative to openings in end caps, and thereby actuate the valve to achieve a desired functional mode. Thus, fluid communication is allowed between an end cap opening and a cylinder channel only if they are in alignment. The syringes depicted in FIGS. 1 and 2 are not all positioned in the same orientation, illustrating their rotational mobility, and illustrating that each syringe is the actuator of rotation of its associated valve.

In some embodiments, valve cylinders are molded of a first plastic material and end caps are molded of second plastic material to be assembled by press fit assembly, with a fluid tight seal present between the cylinder ends and sides and the end cap walls. As shown, the valve end caps are affixed to a wide base 93 to allow single-handed actuation of the valves using the syringes as lever arms. As shown, all four valves are affixed to a single base, as is depicted in FIGS. 1 and 2. Any valve or valve section depicted in other figures may be attached to a base or other support structure.

Figure 3A:
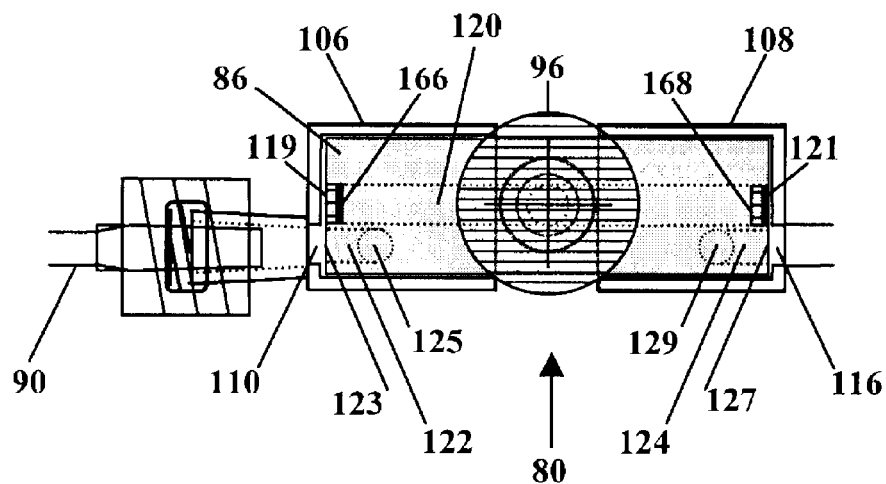
FIG. 3A illustrates detail of a front elevational view of the flush valve in drip mode.
Figure 3B:
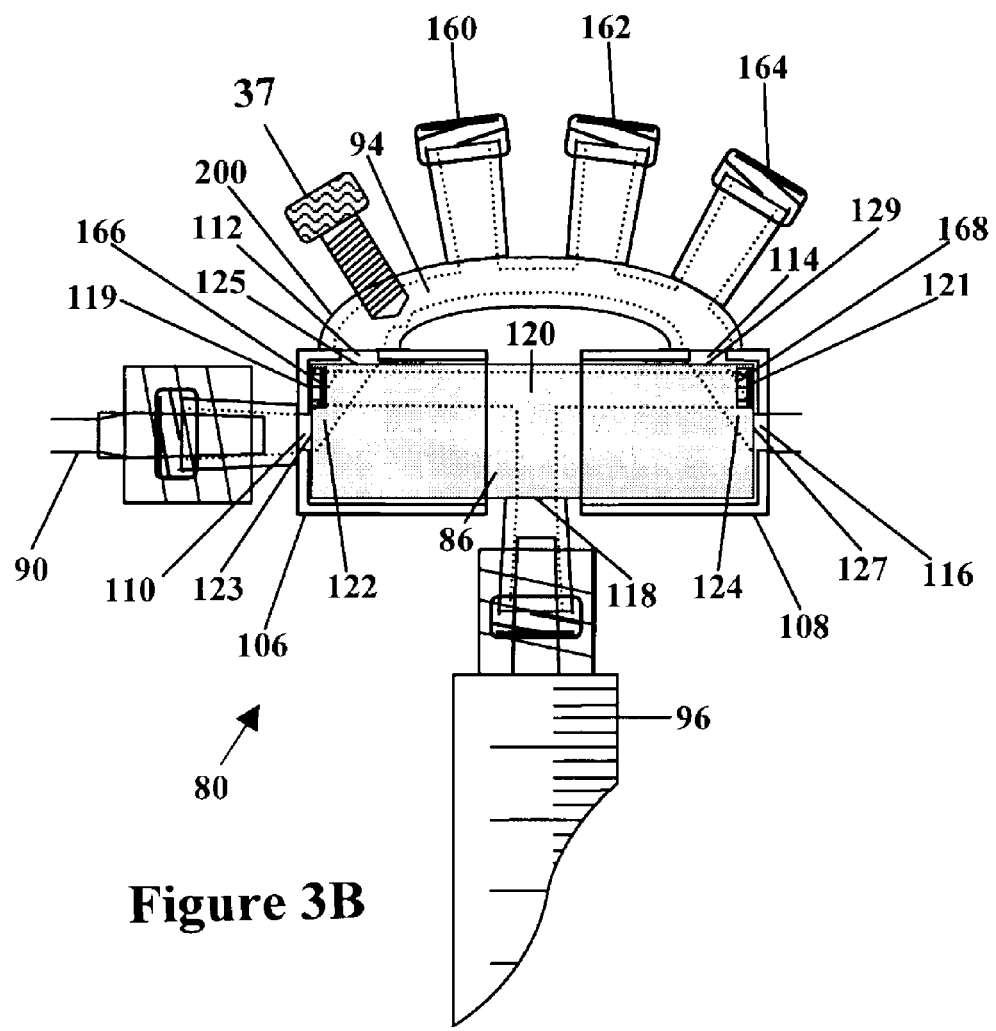
FIG. 3B illustrates detail of a top view of the flush valve in drip mode.
Figure 4:
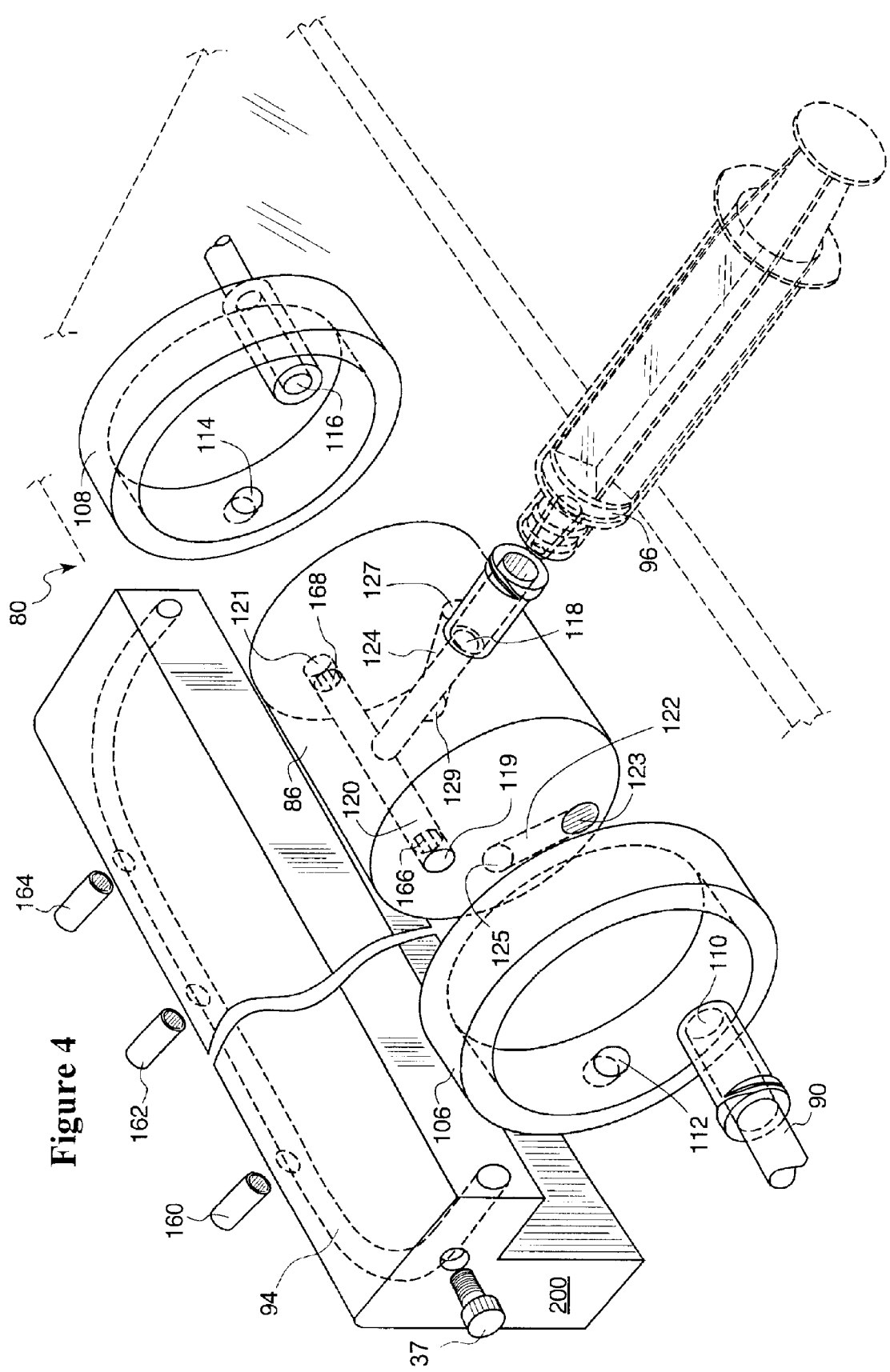
FIG. 4 illustrates an exploded perspective view of the flush valve in drip mode.
Figure 5:
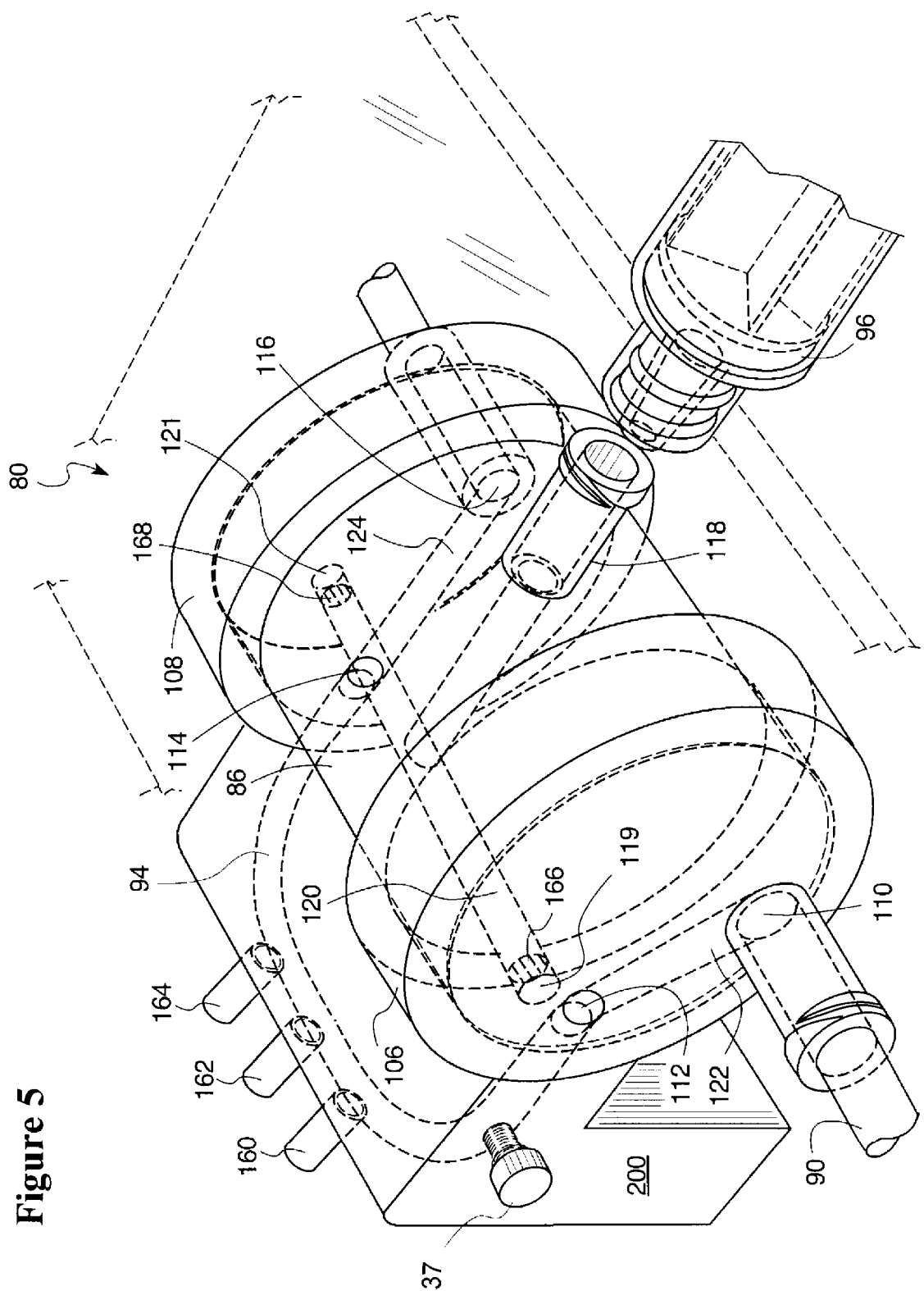
FIG. 5 illustrates a perspective view of the flush valve in drip mode.

FIGS. 3A and 3B depict the flush valve 80 from the front and top, respectively, as in FIGS. 1 and 2, but in greater detail. FIGS. 4 and 5 show exploded and unexploded perspective views, respectively, of the same flush valve 80. The flush valve 80 includes an upstream end cap 106, a flush cylinder 86, and a downstream end cap 108. The upstream end cap has a first opening 110 and a second opening 112; and the downstream end cap has a first opening 114 and a second opening 116. The flush cylinder has a single port 118 on its side, with an attached female Luer connector, and is in fluid communication with a flush channel 120 which extends bi-directionally to both ends of the flush cylinder, from an upstream opening 119 to a downstream opening 121. Any syringe attached to flush cylinder port 118 is referred to as a flush syringe 96 and is in fluid communication with flush channel 120. Flush cylinder 86 also has two other channels, called an upstream drip channel 122 and a downstream drip channel 124. Upstream drip channel 122 extends from an opening 123 on the upstream end of flush cylinder 86 to an opening 125 on the side of the flush cylinder 86, and downstream drip channel 124 extends from an opening 129 on the side of flush cylinder 86 to an opening 127 on the downstream end of the flush cylinder 86. Flush channel 120 is not in fluid communication with upstream drip channel 122 or downstream drip channel 124, regardless of the selected mode of flush valve.

Figure 6:
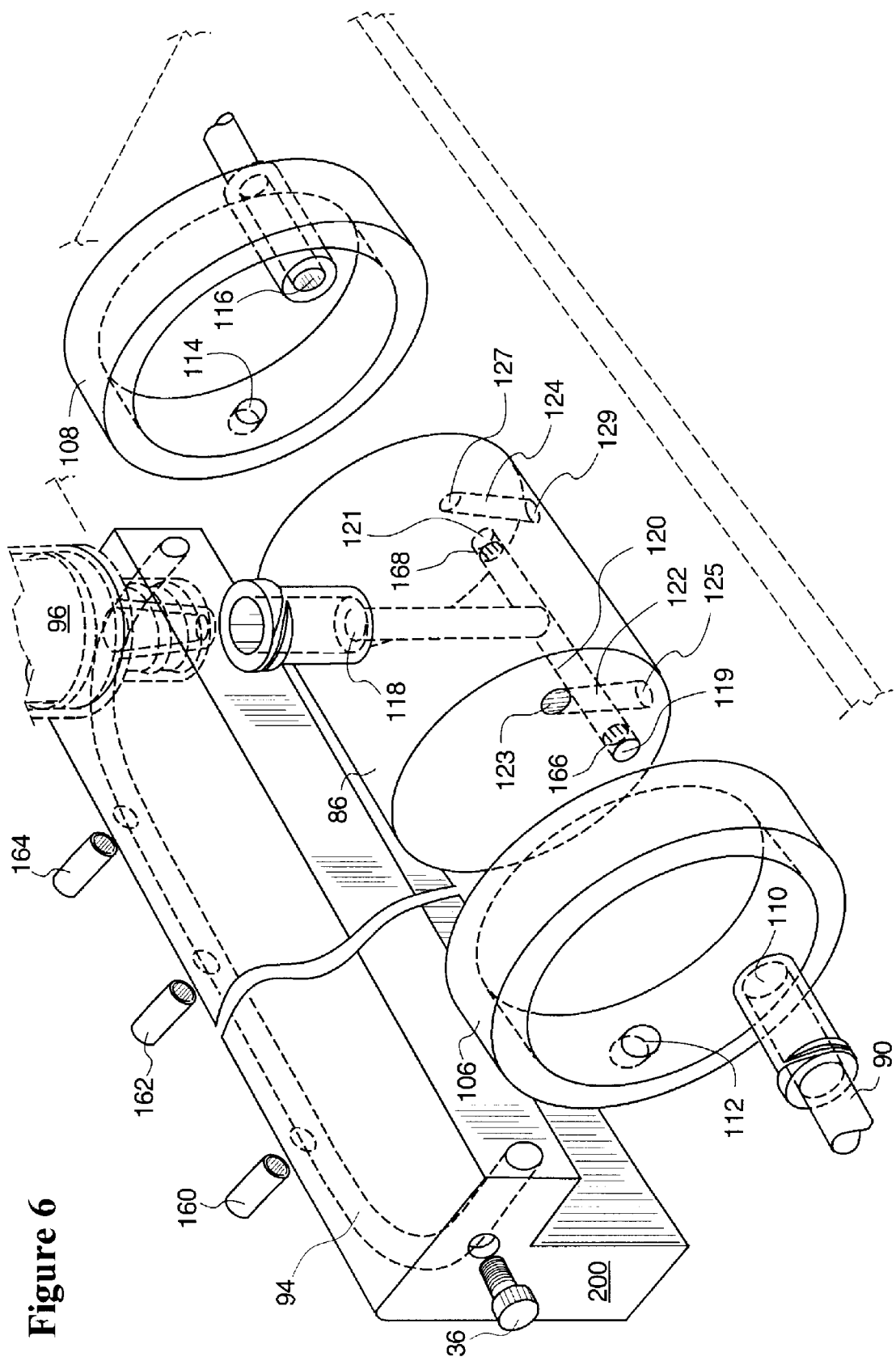
FIG. 6 illustrates an exploded perspective view of the flush valve in flush mode.

Flush valve 80 has two functional modes depending on the rotational position of flush cylinder 86: a drip mode and a flush mode. FIGS. 1, 2, 3A, 3B, 4, and 5 depict the flush valve in drip mode, with FIG. 6 showing an exploded view. In drip mode, flush syringe 96 resides in a horizontal position, parallel with the plane of base 93. This causes openings 123 and 125 of upstream drip channel 122 to align with upstream end cap openings 110 and 112, respectively, and openings 127 and 129 of downstream drip channel 124 to align with openings 116 and 114, respectively. Drip mode establishes a fluid path, in which fluid travels from upstream conduit 90 through first opening 110, into upstream drip channel 122, through second opening 112, into midstream conduit 94, through opening 114, through opening 129, into downstream drip channel 124, through opening 127, through opening 116, and onward to the patient.

Drip mode can be used whenever continuous (drip) infusion is needed, whether deriving from the main IV fluid reservoir 20, auxiliary infusion 36, or both. Drip mode permits standard modifications to the continuous fluid stream. One of these modifications is regulation of flow rate using a threaded screw valve 37 that variably regulates flow rate through the midstream conduit depending on the rotational position of the threaded screw Another modification is the introduction of auxiliary IV fluid from reservoirs 36 by way of ports 160, 162, and 164. In some embodiments, ports 160, 162, and 164 contain integral gravity-fed one-way check valves (similar to those manufactured by Quest Medical, Inc. Allen, Tex.) to prevent retrograde flow, allowing only unidirectional flow from auxiliary IV fluid reservoirs 36 into midstream conduit 94. Screw valve 37 can eliminate the need for flow regulation elsewhere in the system, hence the absence of a roller clamp from upstream conduit 90 in FIGS. 1 and 2. The purpose of locating a flow regulator within the midstream conduit is to isolate its function and thereby provide flush syringe 96 with unimpeded, full-bore access to the main IV reservoir while the valve is in flush mode.

The flush mode of flush valve 80 is shown in FIG. 6 as an exploded perspective view. Flush mode is used to achieve rapid flushing of downstream conduit 104 using flush syringe 96. As shown, flush mode is activated when flush syringe 96 is positioned perpendicular to base 93, aligning flush channel opening 119 with upstream end cap opening 110 and aligning flush channel opening 121 with downstream end cap opening 116, simultaneously causing midstream conduit 94 to become un-aligned from upstream drip channel 122 and downstream drip channel 124. Flush mode puts flush syringe 96 in fluid communication with upstream conduit 90 and with downstream conduit 104. Flush syringe 96 is filled by withdrawing the syringe plunger, thereby aspirating fluid from main IV fluid reservoir 20, and is emptied by depressing the syringe plunger, thereby forcing syringe contents into downstream conduit 104.

The function of flush syringe 96 is facilitated by the presence inside flush channel 120 of two pressure-activated, one-way check valves (similar to those manufactured by Quest Medical, Inc. Allen, Tex.). An upstream check valve 166 is located on the end closest to upstream opening 119 and a downstream check valve 168 is located on the end closest to downstream opening 121. The function of upstream check valve 166 is to prevent fluid in the flush channel from entering upstream conduit 90. The function of downstream check valve 168 is to prevent fluid in downstream conduit 104 from entering the flush channel. Pressure-activated check valves 166 and 168 require a sufficiently high pressure differential across the valves to open, such that a gravity-fed infusion would not cause the valves to open. Therefore, with flush valve 80 in flush mode but with no force applied to the plunger of flush syringe 96, no flow would occur from the upstream fluid reservoir through the flush valve. Only with force applied upward or downward on flush syringe 96 plunger would fluid flow through openings 119 or 121, respectively. Thus, fluid can be aspirated from the upstream conduit 90 by withdrawing the plunger of flush syringe 96, but not from downstream conduit 104 because of downstream check valve 168. Similarly, fluid is forced into downstream conduit 104 by depressing the plunger of flush syringe 96, but not into upstream conduit 90 because of the presence of check valve 166. Thus, flush mode allows syringe 96 to act as a pump by withdrawing and depressing its plunger, causing fluid to move unidirectionally through flush channel 120. In neither drip mode nor flush mode does flush syringe 96 communicate with midstream conduit 94.

The midstream conduit 94 allows an infusion fluid stream to be mutually exclusive from a flushing stream, as shown, by providing the infusion fluid stream in parallel configuration with the flushing stream. Having two or more mutually exclusive fluid streams within one valve allows modification of one stream without affecting another. This is important, for example, when IV requirements dictate certain modifications to the fluid stream which are undesirable when the IV system is called upon to function in a different mode. For example, common IV fluid modifications include regulation of flow rate and the introduction of auxiliary infusions; however, these modifications can hinder efficient flushing of the line. Flush valve 80 facilitates these functions by sequestering those modifications in a separate fluid channel. Moreover, flush valve 80 simplifies the process by allowing rapid alternation between mutually exclusive fluid streams with a single motion, using the syringe as an actuator handle.

As shown, drip mode allows regulation of flow rate using screw valve 37, and the introduction of auxiliary IV fluid by way of ports 160, 162, and 164, but keeps flush channel 122 unaligned with any openings because its openings 119 and 121 face the upstream end cap 106 and downstream end cap 108, respectively, in a fluid-tight relationship. Conversely, flush mode aligns flush channel openings 119 and 121 with end cap openings 110 and 116 to permit flush syringe filling and emptying, but keeps midstream conduit 94 unaligned with any openings.

As shown, the midstream conduit 94 is a fluid passageway formed inside a solid structure of molded plastic 200; however, in other embodiments, the midstream conduit takes a different form and still achieves the same function. For example, midstream conduit 94 could be formed of flexible plastic tubing extending from upstream end cap opening 112 to downstream end cap opening 114. Such tubing might be fitted with standard IV administration features such as a roller clamp, Y-sites, and/or stopcocks.

Similarly, in other embodiments, the flow controller in the midstream conduit takes a different form than the threaded screw valve 37. For example, a mechanism similar to a roller clamp might be employed. Another approach to flow rate control would be to close completely screw valve 37, so as to prohibit flow from upstream conduit 90 into midstream conduit 94. Then, an auxiliary IV fluid reservoir in fluid communication with the midstream conduit via ports 160, 162, or 164, and perhaps driven by a mechanical pump, can serve as the primary infusion. As a result, the main IV fluid reservoir 20 can function only as a flush reservoir, accessible only by flush syringe 96, and not function as an infusion reservoir. An analog controller such as screw valve 37 need not be used, favoring instead the precision of electronically controlled infusion, but still retaining the advantages of an easy flushing system.

In other embodiments, the midstream conduit is not external to the flush cylinder. Rather, the midstream conduit can be integral to the flush cylinder, formed as a channel through the cylinder. Such a midstream conduit would be subjected to flow regulation and auxiliary fluid introduction just as described above, but those features would rotate along with the cylinder as the valve is actuated. Just as described above, the openings at the ends of the midstream conduit can come into alignment with end cap openings only in a specific rotational position of the flush cylinder.

Referring now to one of the injection valves 82 wherein the others, if used, are identical, three are shown in FIGS. 1 and 2, labeled 82a, 82b, and 82c. Each consists of a cylindrical valve element 88 which rotates within an upstream end cap 130 and a downstream end cap 132. In FIGS. 1 and 2, one of the three injection valves, 82b, is shown in injection mode; that is, with cylinder 88 positioned rotationally such that the attached syringe 98 is perpendicular to base 93. Injection valves 82a and 82c are shown in drip mode; that is, with their cylinders 88 positioned rotationally such that their attached syringes 98 are parallel to base 93.

Figures 7, 8:
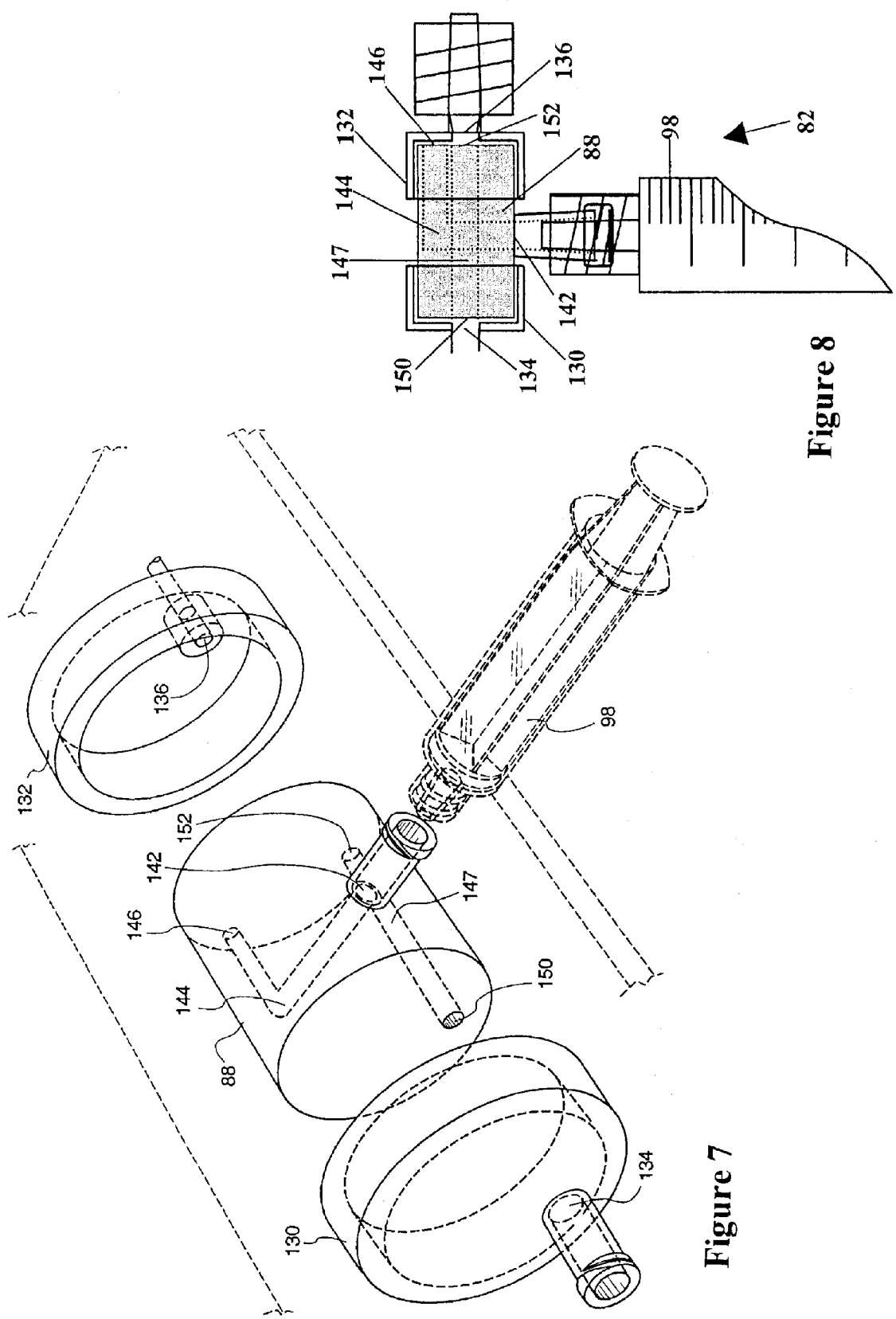
FIG. 7 illustrates an exploded perspective view of the injection valve in drip mode.
FIG. 8 illustrates detail of a top view of the injection valve in drip mode.

FIGS. 7 and 8 show injection valve 82 in drip mode, with FIG. 7 being an exploded perspective view and FIG. 8 being a top view. Each end cap has an opening through which fluid may move only if aligned with an opening in the injection cylinder 88. Upstream end cap 130 has an opening 134 and downstream end cap 132 has an opening 136. Injection cylinder 88 has a port 142 on its side, with an attached female Luer connector, and fluidly communicates with an injection channel 144. Any syringe attached to port 142 is called an injection syringe 98. The injection syringe is in fluid communication with injection channel 144, which extends unidirectionally to an opening 146 at the downstream end of injection cylinder 88. Injection cylinder 88 has one other channel, called drip channel 147 which is a linear conduit, parallel with the longitudinal axis of the injection cylinder, extending from an opening 150 at the upstream end of injection cylinder 88 to an opening 152 at the downstream end of injection cylinder 88.

The injection valve has two functional modes, drip mode and injection mode, depending on the rotational position of the injection cylinder. In drip mode, the injection syringe is positioned parallel to the plane of base 93, as seen with valves 82a and 82c in FIGS. 1 and 2. This rotational position causes openings 150 and 152 of drip channel 147 to align with end cap openings 134 and 136 respectively. Drip mode allows fluid to be conducted into opening 134, through drip channel 147, out opening 136, and into the next injection valve, if one is present, and then into downstream conduit 104. Drip mode does not allow fluid communication between injection syringe 98 and the patient because opening 146 of injection channel 144 is not aligned with any end cap opening.

Figure 9:
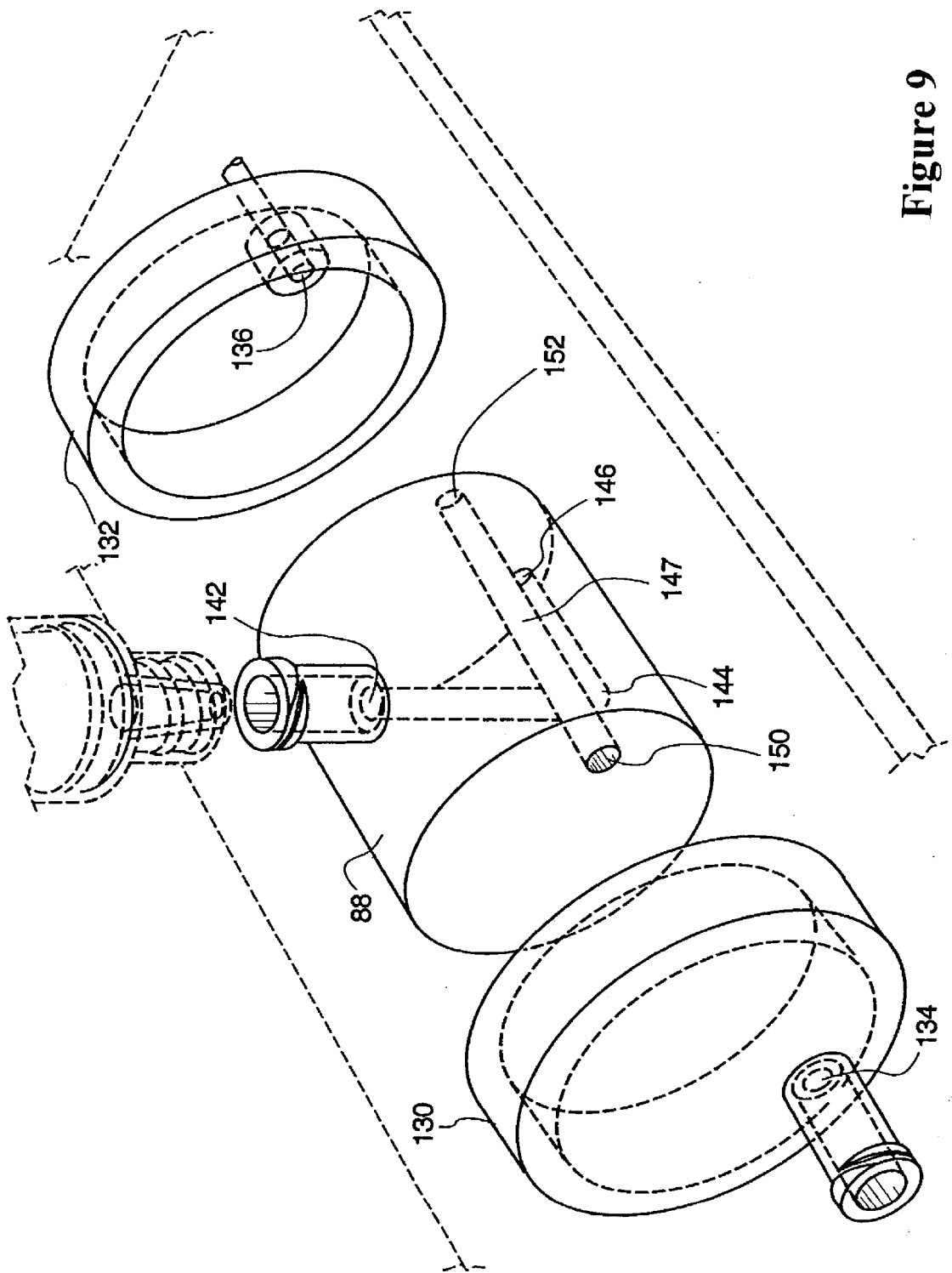
FIG. 9 illustrates an exploded perspective view of the injection valve in injection mode.

FIG. 9 shows an exploded perspective view of the injection valve in injection mode. In injection mode, the injection syringe is positioned perpendicular to the plane of base 93, as seen with valve 82b in FIGS. 1 and 2. This rotational position causes opening 146 in injection channel 144 to align with downstream opening 136 in downstream end cap 132. Injection mode allows fluid to be conducted from injection syringe 98 into injection cylinder port 142, through injection channel 144, out of cylinder opening 146, through end cap opening 136, then into the next injection valve, if one is present, and then into downstream conduit 104. Injection syringe is not in fluid communication with the upstream fluid path in any mode, so there is no risk of upstream dilution or contamination of the contents of the injection syringe.

The embodiments described herein can improve the efficiency of routine and emergency administration of IV fluids. For example, a clinician can inject and then flush medicament to a patient using just one hand with few, fast steps, and with enhanced protection against medication errors. Using certain stopcock technology, the number of two-handed steps to inject a medicament and then flush the line by syringe can be at least ten, with additional steps possibly required to clamp and unclamp auxiliary infusions, to fill a flush syringe from a separate reservoir, or to open a pre-filled flush syringe. The steps involving roller clamps can be particularly laborious and can add significant physical and mental labor to the process, given the frequency with which these tasks may be performed each day. The embodiments described herein can reduce the number of steps to seven, make them all one-handed, and eliminate any roller clamp manipulation. The steps can be, for example, beginning with all valves in drip mode: 1) injection syringe raised to vertical, 2) injection syringe plunger depressed to deliver medicament, 3) injection syringe lowered to horizontal, 4) flush syringe raised to vertical, 5) flush syringe plunger withdrawn to fill, 6) flush syringe plunger depressed to deliver flush, and 7) flush syringe lowered to horizontal.

As described herein, flush valve 80 physically separates two commonly required functions, drip flow and flushing, into mutually exclusive, e.g., parallel, fluid channels—those being midstream conduit 94 and flush channel 120. Either channel can be placed into the fluid stream between upstream conduit 90 and downstream conduit 104 using one hand, by moving flush syringe 96, which serves as a valve actuator. In other embodiments, a flush valve controls flow through multiple mutually exclusive fluid channels, not just two. Each fluid channel can be selected using a similar one-handed movement of a syringe actuator, aligning upstream and downstream openings of the selected channel with upstream and downstream end cap openings. Each channel, e.g., configured in parallel with other channels, can serve a different clinical purpose by virtue of the modifications imposed on the fluid stream along its length. By way of example, one channel can be for flushing with saline, one for flushing with heparinized saline, one for routine infusions, one for emergency infusions, one for IV contrast solution, and so on.

Figure 10:
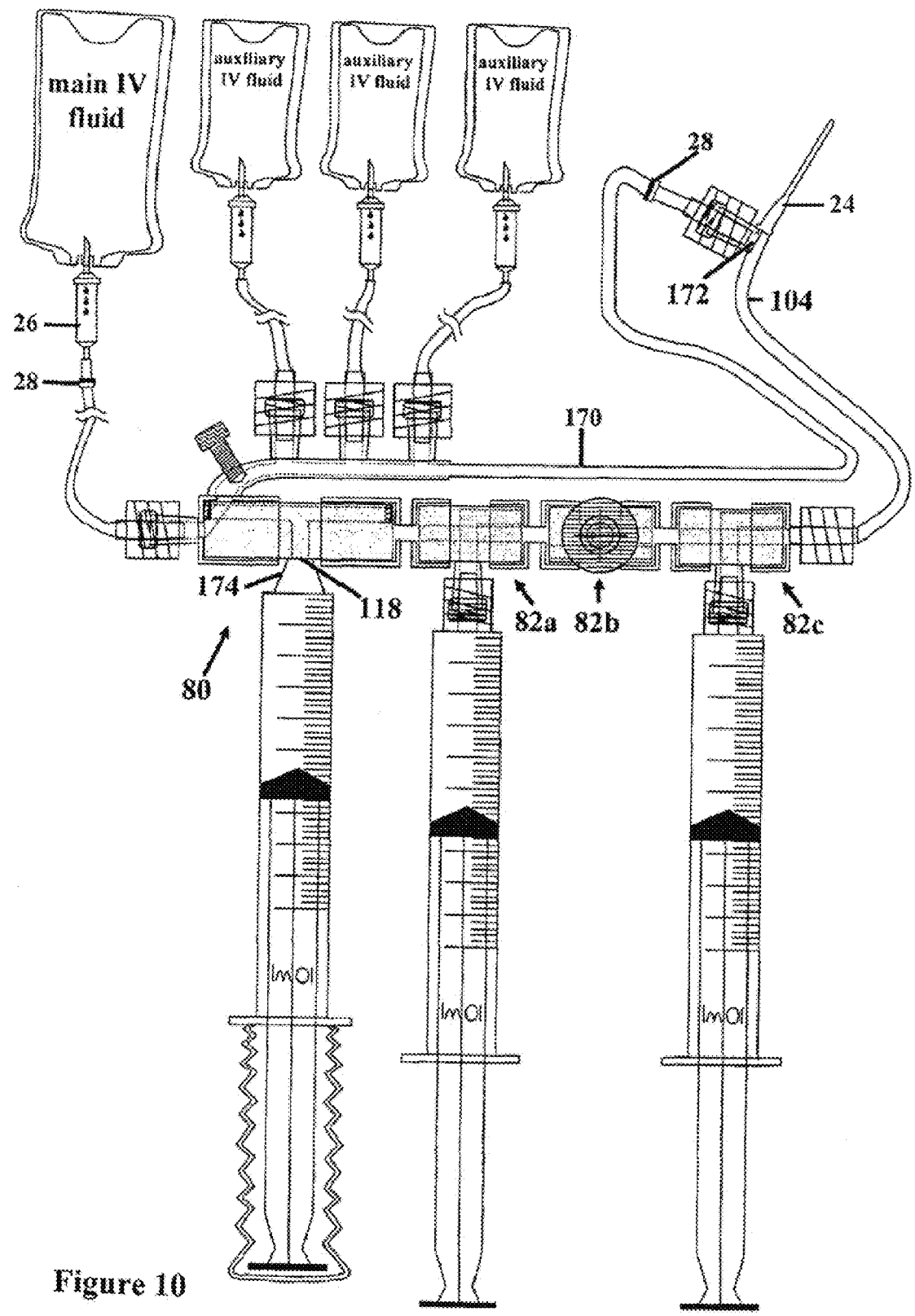
FIG. 10 illustrates a top view of an embodiment of a valve.

In other embodiments, shown in FIG. 10, the flush syringe is permanently fused to the flush cylinder at port 118, unable to be detached without damaging the syringe and/or the cylinder, by way of a rigid connector element 174. This feature would ensure that no clinician mistake the flush cylinder for an injection or infusion port, as no available free attachment port would exist on the cylinder.

FIG. 10 also shows the flush syringe plunger enclosed in an enclosure, as shown, a sealed deformable plastic casing 176. The casing, which can enclose the entire syringe or only a portion of the syringe (e.g., only the plunger), can include a flexible membrane that functions in a bellows-like manner. The casing can ensure a closed, sterile internal environment for the flush syringe, minimizing infection risk over multiple flushing tasks. Such an enclosed flushing system can ensure that the fluid in the flush syringe is as sterile as that in the upstream IV fluid reservoir.

FIG. 10 also shows an elongated midstream conduit 170 re-entering the main fluid stream by joining with downstream conduit 104 near the patient's IV catheter 24 at port 172 instead of re-entering at the flush valve, as does midstream conduit 94 described above. A check valve 28 is shown allowing only unidirectional flow from midstream conduit 170 into downstream conduit 104. The portion of downstream conduit 104 which could contain auxiliary IV fluid is reduced, thereby reducing the amount of auxiliary IV fluid that could be rapidly delivered to the patient as a consequence of giving a fluid bolus through an injection valve or giving a flush through the flush valve. Reducing (e.g., minimizing) the potential for bolus administration of even small quantities of auxiliary IV fluid can be worthwhile because some auxiliary infusion drugs can be harmful, particularly if given too quickly, such as antibiotics, vasoactive pressors, and potassium. The risk is greatest when the concentration of auxiliary fluid in downstream tubing 104 is high, as occurs when drip flow from the main IV fluid reservoir is set to a low rate. These features also serve to quickly re-establish the desired concentration of auxiliary IV infusions entering the patient by drip flow following an injection bolus or a flush maneuver. It is recognized that, as shown, every drug given by an injection syringe be actively flushed using the flush valve, and not flushed passively using drip flow. This is because any administration of medicament through injection valve 82 leaves undelivered a quantity of medicament residing in downstream conduit 104 but upstream of opening 172, which can only be delivered to the patient by actively flushing through the flush valve.

In some embodiments, the components (e.g., plastic components) of the flush valve and injection valves include structural elements to prevent the cylinders from being rotated to any more extreme position than required for drip-flow mode or flush-fill mode or injection mode. This would facilitate switching modes by allowing the clinician simply to move the actuating syringe in an arc until it stopped. For example, if a valve cylinder has multiple parallel fluid channels, as described above, then multiple rotational positions may need to be easily set. To achieve this, another structural element that can be provided is a détente at each cylinder position. This tactile clue or indicator can indicate when the flush syringe is in the proper rotational position. Such structural elements can include a nub on the surface of the valve cylinder which, when it encounters a small depression in the end cap during rotation, would serve to promote stopping of rotation, but which can be easily overcome by further force to rotate the syringe to other positions.

In some embodiments, in association with the valve systems described herein, a bracket is included that can hold base 93 tightly so as to immobilize the valve end caps for easier valve cylinder rotation. Such a bracket can be conveniently attached to an IV pole, desk, or hospital bed. Attachment using an adhesive backing on the base is another alternative. Yet in other embodiments, flush valve 80 and/or injection valve 82 are not affixed to any base, but supported only by their upstream and downstream attachments to the IV tubing.

The flush valves described herein can be used without using the injection valves in some embodiments. For example, the flush valves can be placed upstream of any type of injection port including, but not limited to, Y-sites and four-way stopcocks to achieve flushing of downstream tubing in a manner similar to that described above. Thus, one could administer a bolus of fluid to the patient not using the injection valve 82 but still retain the advantages of the flush valve 80. Also, the injection valve can be used without using the flush valve. For example, one or more injection valves can be used in an intravenous line to achieve bolus dosing of medicament in a manner similar to that described above but without the presence of the flush valve upstream.

The number of injection valves present downstream of the flush valve can be anywhere from none to many, depending on the needs of the user. In some settings, such as for a patient with uncomplicated needs, it may be desirable to have one flush valve and one injection valve present on the base. In other settings, such as for patients in the ICU or operating room, it may be desirable to have one flush valve and two or more injection valves. As shown above, three injection valves are presented to facilitate the description. In some embodiments, the function of injection valves 82 is achieved by other injection ports, such as, for example, four-way stopcocks and/or Y-sites. Flush valve 80 can function upstream of various types of injection ports, not only injection valve(s) 82.

Still other embodiments are within the scope of the claims.

What is claimed is:

1. An apparatus for directing fluid flow to a subject, the apparatus comprising:
    a first valve sized and dimensioned for directing the flow of intravenous fluid comprising
        an inlet capable of being in fluid communication with an intravenous fluid source;
        an outlet capable of being in fluid communication with the inlet
        a first port to be in fluid communication with a flush syringe; and
        two unidirectional valves,
    wherein the first valve has an axis of rotation and is capable of being in a first mode in which the inlet is in fluid communication with the outlet through a first flow path, and a second mode in which the inlet is in fluid communication with the outlet through a second flow path isolated from the first flow path, and
    the two unidirectional valves are along the second flow path, the first port is in fluid communication with the second flow path and is between the two unidirectional valves, and the flush syringe, when coupled to the first port, provides a first valve handle for selecting between the first mode and second mode by pivotal rotation of a longitudinal axis of the flush syringe in an arc about the axis of rotation of the first valve.

2. The apparatus of claim 1, wherein the first valve is associated with a base, and the flush syringe is capable of pivoting relative to the base.

3. The apparatus of claim 1, wherein the two unidirectional valves are capable of being between the inlet and the outlet along the second flow path.

4. The apparatus of claim 1, wherein the first valve further comprises a controller capable of controlling fluid flow through the first flow path.

5. The apparatus of claim 1, wherein the first flow path is capable of being in fluid communication with a second fluid source.

6. The apparatus of claim 1, wherein the first valve comprises a body comprising at least a portion of the first flow path, at least a portion of the second flow path, and the two unidirectional valves, and rotation of the body allows the first valve to be in a selected mode.

7. The apparatus of claim 1, wherein the first valve comprises a body comprising:
    a first channel,
    a second channel, and
    a third channel containing the two unidirectional valves, the first, second and third channels capable of being isolated from each other,
    wherein, in the first mode, the first channel, the second channel, the inlet, the outlet, and the first flow path are in fluid communication, and
    in the second mode, the third channel, the inlet, and the outlet are in fluid communication.

8. The apparatus of claim 1, wherein the first valve further comprises a tactile indicator capable of denoting a selected mode of the first valve.

9. The apparatus of claim 1, further comprising:
    a second valve capable of being in fluid communication with the first valve, the second valve comprising
    a second inlet,
    a second outlet capable of being in fluid communication with the second inlet, and
    a port,
    wherein the second valve is capable of being in a third mode in which the second inlet is capable of being in fluid communication with the second outlet, and a fourth mode in which the second outlet is capable of being in fluid communication with the port.

10. The apparatus of claim 9, wherein the second valve is configured to engage with a fluid injector, and the injector and the port are capable of being in fluid communication.

11. The apparatus of claim 9, wherein the second valve is associated with a base, and the injector is capable of pivoting relative to the base.

12. The apparatus of claim 9, wherein the first and second valves are secured to a base.

13. The apparatus of claim 1, further comprises:
    an intravenous catheter capable of being in fluid communication with the outlet.

14. An apparatus for directing intravenous fluid flow to a subject, the apparatus comprising:
    a first valve sized and dimensioned for directing the flow of intravenous fluid comprising
        an inlet capable of being in fluid communication with an intravenous fluid source;
        an outlet capable of being in fluid communication with the inlet;
        a first port adapted to be in fluid communication with a flush syringe; and
        two unidirectional valves,
    wherein the first valve has an axis of rotation and is capable of being in a first mode in which the inlet is in fluid communication with the outlet through a first flow path, and a second mode in which the inlet is in fluid communication with the outlet through a second flow path isolated from the first flow path, the first port is in fluid communication with the second flow path and is between the two unidirectional valves, and the flush syringe, when coupled to the first port, provides a first valve handle for selecting between the first mode and second mode by pivotal rotation of a longitudinal axis of the flush syringe in an arc about the axis of rotation of the first valve, and
    the two unidirectional valves are along the second flow path; and
    a second valve sized and dimensioned for directing the flow of intravenous fluid capable of being in fluid communication with the first valve, the second valve comprising
    a second inlet,
    a second outlet capable of being in fluid communication with the second inlet, and
    a second port adapted to be in fluid communication with a medicament injection syringe,
    wherein the second valve has an axis of rotation and is capable of being in a third mode in which the second inlet is capable of being in fluid communication with the second outlet, and a fourth mode in which the second outlet is capable of being in fluid communication with the second port, and the medicament injection syringe, when coupled to the second port, provides a second valve handle for selecting between the third mode and the fourth mode by pivotal rotation of a longitudinal axis of the medicament injection syringe in an arc about the axis of the rotation of the second valve, wherein the first flow path extends from the inlet of the first valve to a position downstream of the second outlet of the second valve when the first valve is in the second mode.

15. The apparatus of claim 14, further comprising a unidirectional valve along the first flow path.

16. The apparatus of claim 14, wherein the first valve further comprises a port in fluid communication with the second flow path between the two unidirectional valves.

17. The apparatus of claim 16, wherein the port is adapted to be in fluid communication with an injector.

18. The apparatus of claim 17, wherein the first valve is associated with a base, and the injector is capable pivoting relative to the base.

19. The apparatus of claim 14, wherein the two unidirectional valves are capable of being between the inlet and the outlet along the second flow path.

20. The apparatus of claim 14, wherein the first valve further comprises a controller capable of controlling fluid flow through the first flow path.

21. The apparatus of claim 14, wherein the first flow path is capable of being in fluid communication with a second fluid source.

22. The apparatus of claim 14, wherein the first valve comprises a body comprising at least a portion of the first flow path, at least a portion of the second flow path, and the two unilateral valves, and rotation of the body allows the first valve to be in a selected mode.

23. The apparatus of claim 14, wherein the first valve further comprises a tactile indicator capable of denoting a selected mode of the first valve.

24. An apparatus for directing intravenous fluid flow to a subject, the apparatus comprising:

a first valve sized and dimensioned for directing the flow of intravenous fluid comprising an inlet capable of being in fluid communication with an intravenous fluid source;

an outlet capable of being in fluid communication with the inlet;

a first port adapted to be in fluid communication with a syringe; and two unidirectional valves, wherein the first valve has an axis of rotation and is capable of being in a first mode in which the inlet is in fluid communication with the outlet through a first flow path, and a second mode in which the inlet is in fluid communication with the outlet through a second flow path isolated from the first flow path, the first port is in fluid communication with the second flow path and is between the two unidirectional valves, and the syringe, when coupled to the first port, provides a first valve handle for selecting between the first mode and second mode by rotation of the syringe about the axis of rotation of the first valve, and the two unidirectional valves are along the second flow path; and a second valve sized and dimensioned for directing the flow of intravenous fluid capable of being in fluid communication with the first valve, the second valve comprising a second inlet, a second outlet capable of being in fluid communication with the second inlet, and a second port adapted to be in fluid communication with a second syringe, wherein the second valve has an axis of rotation and is capable of being in a third mode in which the second inlet is capable of being in fluid communication with the second outlet, and a fourth mode in which the second outlet is capable of being in fluid communication with the second port, and the second syringe, when coupled to the second port, provides a second valve handle for selecting between the third mode and the fourth mode by rotation of the second syringe about the axis of the rotation of the second valve, wherein the first flow path extends from the inlet of the first valve to a position downstream of the second outlet of the second valve when the first valve is in the second mode.

* * * * *